United States Patent
Yokochi et al.

(10) Patent No.: US 6,461,839 B2
(45) Date of Patent: Oct. 8, 2002

(54) METHOD OF PRODUCING A POLYUNSATURATED FATTY ACID CONTAINING CULTURE AND POLYUNSATURATED FATTY ACID CONTAINING OIL USING MICROORGANISMS

(75) Inventors: Toshihiro Yokochi; Toro Nakahara; Masakazu Yamaoka, all of Ibaraki; Ryuichiro Kurane, Chiba, all of (JP)

(73) Assignee: Agency of Industrial Science and Technology, Tokyo (JP)

(*) Notice: Subject to any disclaimer, the term of this patent is extended or adjusted under 35 U.S.C. 154(b) by 0 days.

(21) Appl. No.: 09/749,035

(22) Filed: Dec. 28, 2000

(65) Prior Publication Data

US 2001/0041358 A1 Nov. 15, 2001

(30) Foreign Application Priority Data

Mar. 30, 2000 (JP) .......................................... 2000-94441

(51) Int. Cl.$^7$ .............................. C12P 7/64; C12N 1/26; C12N 1/20
(52) U.S. Cl. ..................... 435/134; 435/248; 435/253.6
(58) Field of Search ................................. 435/134, 248, 435/253.6

(56) References Cited

FOREIGN PATENT DOCUMENTS

JP 2976027 2/2000

OTHER PUBLICATIONS

Nakahara, T., and Yokochi, T. 1999. Production of DHA by Labyrinthula cells. Seibutsu Kogaku Kaishi, 77(4): 150–153 (ABSTRACT).*
Yokochi, T. Polyunsaturated fatty acids production by microbial cultivation. 1997. Nihon Yukagakkaishi 46(10), 1275–1280 (ABSTRACT).*
Porter, "Phylum Labyrinthulomycota", Hand*book of Protoctista*, Jones and Barlett Publishers, pp. 388–398 (1990).
Nakahara et al., "Production of DHA by Labyrinthulomycota," *Seibutsu Kogaku Kaishi*, vol. 77, 4, pp. 150–153 (1999).
Partial English Translation of Nakahara et al., "Production of DHA by Labyrinthulomycota," *Seibutsu Kogaku Kaishi*, vol. 77, 4, pp. 150–153 (1999).
Sakata et al., "Colony Formation and Fatty Acid Composition of Marine Labyrinthulid Isolates Grown on Agar Media," *Fisheries Science*, vol. 66, pp. 84–90 (2000).
Yokochi, "Polyunsaturated Fatty Acids Production by Microbial Cultivation." *Nihon Yukagakkaishi*, 46, vol. 10, pp. 1275–1280 (1997).
Partial English Translation of Yokochi, "Polyunsaturated Fatty Acids Production by Microbial Cultivation." *Nihon Yukagakkaisi*, 46, vol. 10, pp. 1275–1280 (1997).
Yokochi et al., "A New Isolation Method for Labyrinthulids Using a Bacterium, Psychrobacter Phenylpyruvicus," *Mar. Biotechnol.*, vol. 3, pp. 68–73 (2001).

* cited by examiner

*Primary Examiner*—Christopher R. Tate
*Assistant Examiner*—Kailash C. Srivastava
(74) *Attorney, Agent, or Firm*—Finnegan, Henderson, Farabow, Garrett & Dunner, L.L.P.

(57) ABSTRACT

Present invention provides a method to efficiently manufacture an oil-containing product including long chain polyunsaturated fatty acid, or a high added value oil containing long chain polyunsaturated fatty acids. The method comprises culturing a microorganism belonging to the Genus Labyrinthula. The Labyrinthula microorganism is cultured in a medium containing oil or fatty acid as a carbon source, and the produced long chain polyunsaturated fatty acid is recovered from the culture. With the present invention, it is possible to efficiently produce from the vegetable oil and the like, an oil containing product comprising long chain polyunsaturated fatty acids such as docosahexanoic acid having a carbon number of 20 or more, and two or more unsaturated bonds, or an oil containing the long chain polyunsaturated fatty acid. Further, the method of the present invention may be used to reform oil by converting the plant oil and like to high added value oil containing the long chain polyunsaturated fatty acid.

4 Claims, No Drawings

METHOD OF PRODUCING A POLYUNSATURATED FATTY ACID CONTAINING CULTURE AND POLYUNSATURATED FATTY ACID CONTAINING OIL USING MICROORGANISMS

FIELD OF THE INVENTION

The present invention relates to a microorganism belonging to the genus Labyrinthula having the ability to produce long chain polyunsaturated fatty acids, a culture of the microorganism, and a method of producing long chain polyunsaturated fatty acids having a carbon number of 20 or more and having two or more unsaturated bonds (herein, polyunsaturated fatty acid having two or more unsaturated bonds is referred to as "PUFA", and the above-mentioned polyunsaturated fatty acid having a chain length of 20 or more is referred to as "LCPUFA") using the microorganism.

BACKGROUND OF THE INVENTION

LCPUFAs such as arachidonic acid (AA), eicosapentaenoic acid (EPA) and docosahexaenoic acid (DHA) have attracted attention for their various physiological activities within, and recently their use in functional foods, and the pharmaceutical field. However, these LCPUFAS are not contained at all in general vegetable oils, only DHA and EPA are found in fish oils such as sardine and tuna. Since various components of LCPUFAs have characteristic physiological functions, regulation of their compositions and contents are important for application in various fields. However, as a technique for this purpose, there is only a method employing enzymes for concentration and purification of DHA from fish oil, and there is no other converting means for regulation of its composition and content. Under these circumstances, there is a need to develop a variety of supply sources of LCPUFA-containing oil having a characteristic LCPUFA composition. One of these important methods is a method of production using microorganisms. Until now, in the production of γ-linolenic acid, arachidonic acid and the like which are not present in general vegetable oil, a method comprising culturing Mortierella and collecting oil containing these PUFAs from these molds, has been employed. Further, methods have been developed which use marine microorganisms such as Thraustochytrium or Schizochytrium for the production of DHA, which is a LCPUFA and the object of the present invention.

In the case where LCPUFA is produced by a microorganism in this manner, a method of culturing where precursor fatty acids or oils are used as carbon sources is promising. Since using an oil or fatty acid which is a PUFA precursor is energetically favorable, there is the possibility that higher production efficiency can be obtained than in the case where sugars such as glucose are used as initial raw materials. Further, by converting known vegetable oils such as soybean oil or palm oil into PUFA-containing oil, the added value of these oils can be greatly increased. It may also be possible to modify physical properties such as boiling point by altering the fatty acid composition.

It has long been known that some microorganisms can be cultured with oil as a carbon source. There are many examples of such cultures of yeast and bacteria and the like. However, the object of these cultures was primarily the microbes themselves, i.e. cultures directed to the production of proteins. It is also known that Mortierella molds have the ability to convert α-linolenic acid, which is a component found in vegetable oil, into eicosapentaenoic acid.

However, until now there has not been found any microorganism having the ability to convert oil or fatty acid as a carbon source, into LCPUFA, having a carbon number of 20 or more and two or more unsaturated bonds, such as DHA. Even with the production method using microorganisms such as Thraustochytrium which have the ability to produce DHA, sugars such as glucose must be used as a carbon source. In the case where oil or fatty acid is used as a carbon source, while these are incorporated by the microorganisms, desaturation or elongation of chain length hardly occurs. As a result, while there is an increase of microbes yielded, there is the disadvantage that the amount of produced LCPUFA including DHA is extremely reduced.

Further, the Labyrinthula of the present invention, does not fundamentally grow other than on the solid surface of a agar medium, and need to be monoxenic culture with other bacteria or yeast as feed for the sub-cubture. Since no effective method of culturing able to be used in the production of LCPUFA such as DHA has yet been found, screening for a strain with high LCPUFA productivity or examination of culture conditions for LCPUFA production has not been conducted until now.

Conventionally, there has been no microorganisms which can grow with oil as a carbon source, as well as can convert the oil incorporated by the microorganism to LCPUFA including DHA, nor a method for culturing such a microorganism. Thus, the object of this invention is to provide a microorganism having the ability to convert vegetable oil and the like which does not contain LCPUFA into oil containing LCPUFA such as DHA, a method of culturing this microorganism, and a method of producing LCPUFA-containing oil.

BRIEF SUMMARY OF THE INVENTION

The present inventors examined the ecological characteristics etc. of Labyrinthula among marine fungi as one microorganism which comprises LCPUFA such as DHA, and at the same time conducted research on an isolation/culture method exploiting these ecological characteristics. As a result, with respect to Labyrinthula, which is conventionally difficult to grow efficiently and stably, the inventors have found a efficient and selective isolation method of Labyrinthula from a variety of isolation sources such as seaweed and the fallen leaves of mangroves, wherein the method involves placing sample leaves on agar medium, on which Moraxella marine bacterium had been spread and grown. The inventors have already obtained Japanese Patent No. 2976027 in respect of this method. Further, at the same time, the inventors examined the application of oil and the like as a carbon source as a method for efficiently producing LCPUFA including DHA, and have studied the culture with oil and the like of various marine fungi capable of producing DHA including Labyrinthula obtained from various isolation sources, as well as examined the screening and culture conditions of a microorganism having the ability to convert such carbon source to oil which contains LCPUFA such as DHA, thereby completing the present invention.

That is, one aspect of the present invention is a microorganism belonging to the genus Labyrinthula that is able to be cultured with oil or fatty acid as a carbon source, and has the ability to produce long chain polyunsaturated fatty acid. Labyrinthula sp S3-2 is provided as a concrete example of this microorganism.

Further, another aspect of the present invention is a culture of microorganisms belonging to the genus Labyrinthula that can be obtained by culturing the above microorganism in a medium containing oil or fatty acid as a carbon source.

Further, another aspect of the present invention is a method for producing long chain polyunsaturated fatty acid comprising the steps of culturing the above microorganism in a medium containing oil or fatty acid as a carbon source, and collecting long chain polyunsaturated fatty acid from the culture.

Further, another aspect of the present invention is a method for reforming conventional plant oils by converting the oil to long chain polyunsaturated fatty acid by culturing a microorganism of the genus Labyrinthula, with oil as a carbon source.

The above-mentioned long chain polyunsaturated fatty acid includes fatty acids having a carbon number of 20 or more and two or more unsaturated bonds, for example, DHA.

DETAILED DESCRIPTION OF THE INVENTION

1. The Microorganism to be Used in the Present Invention

The microorganism to be used in the present invention is an isolated strain of Labyrinthula collected by the method described hereafter, and may be any strain which will grow with oil or fatty acid as a carbon source and has the ability to convert these to LCPUFA including DHA.

The oils as carbon source includes soybean oil, palm oil, olive oil, safflower oil and the like and fatty acids includes saturated and unsaturated fatty acids such as miristic acid, stearic acid, oleic acid, linoleic acid and the like, as well as esters thereof such as ethyl ester.

2. Method for Isolating Labyrinthula

It is known that Labyrinthula is distributed broadly throughout the marine environment from the tropics to polar regions. As isolation sources therefor, sea water and various seaweed or seagrass such as eelgrass, the fallen leaves of plants abundant on the coast such as mangrove forests, various benthic animals, pieces of wood, silt, various organic matter collected from the sea or the coast can be used. However considering the distribution density of Labyrinthula and growth activity of the isolated strain, leaf fragments of eelgrass and fallen mangrove leaves of *Bruguiera gymnorrhiza* and the like collected from tropical/subtropical sea area are preferable isolation sources. These can be collected as isolation sources by the below-indicated method (See Japanese Patent No. 2976027).

i) Preparation of Agar Medium

The medium to be used for the isolation and culture of Labyrinthula is prepared as follows. That is, a medium is prepared with 0–10 g of glucose, yeast extract, peptone and the like as a suitable nutrition source and 5–20 g of agar in 1 liter of natural seawater or artificial seawater, sterilized with steam, poured into Petri dishes (dishes of 9 cm diameter are often used) such as those used in normal microorganism culture experiments, then allowed to cool and solidify. The concentration of natural seawater or artificial seawater can be regulated to 20 to 100% of the salt concentration of normal seawater, but a concentration of 50 to 90% is preferable for culturing Labyrinthula microorganisms.

ii) Application of bacteria to the agar medium

In order to grow Labyrinthula efficiently, an agar plate medium of the aforementioned capacity on which a bacteria has previously been first applied and cultured is used. The bacteria used here is preferably a marine bacteria, of which Moraxella bacterium (for example, Moraxella sp. LB004 which was deposited at the National Institute of Bioscience and Human-Technology, Agency of Industrial Science and Technology (1–3, Higashi 1-chome, Tsukuba-shi, Ibaraki-ken, Japan) on Dec. 25, 2000, and received Accession No. FERM BP-7412) is a representative marine bacterium for the efficient growth of Labyrinthula. When the concentration of seawater used for preparing the agar plate medium is 50% or less bacteria of terrestrial origin can also be used. The bacteria to be applied are inoculated into a culture liquid previously prepared with glucose (0.1%), peptone (0.05%), yeast extract (0.25%) in 50% concentration of artificial seawater, and cultured with agitation for 2 to 7 days, at a culture temperature of 20–30° C. The culture is performed with culture conditions suitable to the bacteria that are used. 100 microliters each of this bacterial culture liquid is inoculated under sterile conditions onto agar plate mediums prepared in a Petri dish. The liquid is then spread over the surface of each medium with a Conradi rod or the like, or static cultured for 1 to 5 days at a culture temperature of 20 to 30° C., or at room temperature, to allow the bacteria to grow thereon. These are then used in the isolation of the Labyrinthula microorganisms below.

Samples of seagrass, fallen mangrove leaves or the like are cut into fragments of about 1 cm×1 cm, and thereupon, the surface thereof is washed several times with sterilized water. After removing as much as possible of the surface bacteria or mold spores and the like from the water adsorbed to the surface, each fragment is placed onto the center of the agar plate medium on which the above-described Moraxella bacteria have been applied and cultured. This agar plate medium is then incubated at room temperature or a culture temperature of 20 to 30° C. for 2 to 7 days, and the appearance of Labyrinthula microorganisms is microscopically observed. Labyrinthula microorganisms consist of spindle-shaped cells of a length of about 10 $\mu$m, which are strung together like beads or form a clump, spread over the agar plate medium while exhibiting sliding movement. By this movement, radial spreading of the reticular net or fungal hypha from the vicinity of the sample can be observed, and often, within 2 to 5 days it reaches from the centre of the Petri dish where the sample was pasted to the perimeter of this Petri dish. At this time, various bacterium, mold, yeast or the like other than Labyrinthula appear in the sample but their growth is restricted by the Moraxella sp. that were applied. Further, Labyrinthula microorganisms repeat active growth within colonies of Moraxella, extending in an reticular net. Cell clusters of the reticular net reaching to near the rim of the Petri dish are excised together with agar medium (approximately 5 mm×5 mm) and are once more, transferred to the center of the agar plate medium where Moraxella bacteria were applied/cultured. Once more, this agar plate medium is incubated for 2 to 7 days at a room temperature or at 20 to 30 C. By this method or by repetition of this method, isolation of Labyrinthula becomes possible. However, this isolated microorganism is a monoxenic culture with Moraxella bacteria and the like.

iii) Characteristics of the monoxenic culture

This monoxenic culture is readily purified in an agar plate medium containing a suitable amount of antibiotics such as chloramphenicol. However, Labyrinthula in its purified form has extremely low reproductivity on agar plate medium to which horse serum (1%) has been added, some growth can be observed, maintaining the cultured strain as a pure strain, and sub-culturing are difficult. On the other hand, by using an agar plate medium to which marine bacteria such as Moraxella sp. have already been applied, extremely good growth and activity of the fungi can be maintained.

3. Characteristics of Labyrinthula

Labyrinthulas have the following mycological properties, and can be readily distinguished from other microorganisms by microscopic observation for their form and movement.

The vegetative cells of Labyrinthula have a characteristic spindle form and their ectoplasmic network exhibits gliding movement. Two taxonomic orders higher is Labyrinthulomycota which consists of the families Labyrinthulaceae and Thraustochytriceae. It has been reported that Labyrinthulaceae contains one genus Labyrinthula, while Thraustochytriceae contains 7 genera such as Thraustochytrium and Schizochytrium (Handbook of Protoctista, David Porter, 1990). Further, the vegetative cells of Thraustochytriceae are spherical or egg-shaped, and are easily distinguishable from the characteristic spindle form of Labyrinthula. These Labyrinthulomycota, previously classified as fungi, exists widely in the marine environment and grows heterotrophically and was known as marine fungi. Among these, Thraustochytriceae was classified as oomycota whereas Labyrinthulaceae was myxamycota. However, these Labyrinthulomycota generally has a life cycle involving zoospores having two flagella of different length and form, and have recently been incorporated into Heterokontae of chromophyta due to the structure of this zoospore or genetic phylogenetic analysis.

4. Deposited Strain

An isolated strain representative of the present invention is the Labyrinthula sp., S3-2 strain, which was isolated by the above-described method from fallen leaves of Bruguiera gymnorrhiza collected at Ishigaki Island, and deposited at the National Institute of Bioscience and Human-Technology, Agency of Industrial Science and Technology (1-3, Higashi 1-chome, Tsukuba-shi, Ibaraki-ken, Japan) on Mar. 14, 2000, and received Accession No. FERM BP-7090.

Other isolated strains include Labyrinthula sp 714-2, P11-1, P28-1, P37-1, P38-2, and P47-1.

Further the microorganisms used in the oil reforming of the present invention is not limited to the above-mentioned FERM BP-7090, but any strains having mycological properties which are essentially identical to the above described Labyrinthula can be used. LCPUFA-containing oil can be obtained by culturing such a microorganism with oil or fatty acid as a raw material, and after allowing LCPUFA such as DHA to accumulate within this culture, recovering oil from this culture.

5. Oil plate medium

For the Labyrinthula culture having oil or fatty acid as a raw material, a medium of the medium composition used in the isolation/cultivation of the Labyrinthula is prepared, sterilized by steam, and then fatty acid such as oleic acid or linoleic acid, or oil such as soybean oil or palm oil is added to the medium in the amount of 1 g to 20 g per liter, emulsified and dispersed through the medium using an ultrasonicator or the like. The product is then poured into Petri dishes to form an agar plate medium. As a fatty acid or oil, apart from the examples given here, saturated or unsaturated fatty acid such as stearic acid, miristic acid or α-linolenic acid, or esters thereof such as ethyl ester, and natural vegetable oils such as olive oil or safflower oil, or synthetic triglycerides such as triolein can be used. In order to aid dispersion of the oil etc. within the medium, it is effective to first add a suitable amount of surfactant such as Tween-80 to the medium. Further, as nitrogen sources to be added to the medium, organic nitrogen sources such as corn steep liquor, urea, sodium glutamate and inorganic nitrogen sources such as ammonium acetate, ammonium sulfate, ammonium chloride, ammonium nitrate can be used in place of the above-mentioned yeast extract and peptone. As an inorganic salt, potassium phosphate and the like can be suitably incorporated. Further, instead of glucose, sugars such as fructose, saccharose or the like, or glycerol can be used.

6. Method of Culturing

Moraxella sp. which have already been cultured in a known liquid medium prepared with glucose and peptone suitable for the bacteria, for example a liquid medium prepared with glucose (0.1%), peptone (0.05%), yeast extract (0.025%) in 50% salt concentration of artificial sea water, are (firstly) applied and cultured on an oil or fatty acid containing solid medium prepared as above, or even if the bacteria are applied at the time of inoculating Labyrinthula, the effect is equivalent. Using the isolation/culture medium to which Moraxella sp. have been applied and in which Labyrinthula has sufficiently grown, a reticular net of the Labyrinthula spreading, is excised (approx. 5 mm×5 mm), and placed on the center of the oil-containing medium and incubated for 3 to 14 days at a culture temperature of 15 to 30 C. Labyrinthula firstly exhibits spreading of reticular net or fungal hyphae from the inoculated origin within the Moraxella colony, however further intrusion into and active growth within the agar is exhibited on the oil-containing plate. As a result of this, whitely emulsified oil-containing plate gradually increases in transparency accompanied by the growth of Labyrinthula. This is thought to be due to the uptake of the oil emulsified and dispersed within the agar into the cells of the Labyrinthula.

7. Culture product

The agar medium in which the culture has been performed for the prescribed period becomes clogged with Labyrinthula which have grown utilizing the oil. Oil dispersed throughout the medium is incorporated by the microorganisms and thereafter converted to LCPUFA and accumulates within the microorganisms.

Oil content and LCPUFA content of the agar plate medium, being the product of this culture, are determined by excising fragments of the agar on which the Labyrinthula were grown, and analysis of the fatty acid composition was performed by a gas chromatograph in ordinary methods.

8. Recovery of the oil

To recover oil which contains LCPUFA from this culture, after disrupting the cell by ultrasonification or dyno-mill, organic solvent extraction can be performed with, for example, hexane or chloroform or the like.

The oil content was 1-25% weight per 1 g of agar (wet weight), and the LCPUFA content of the oil was 1-25%. The composition of LCPUFA comprises arachidonic acid (AA, 20:4) and eicosapentaenoic acid (EPA, 20:5) having a carbon number of 20, as well as docosatetraenoic acid (DTA, 22:4), docosapentaenoic acid (DPA, 22:5), docosahexaenoic acid (DHA, 22:6) having a carbon number of 22. LCPUFA was not present within the oil used as a raw material, and was formed by the Labyrinthula. These products were not formed at all when Moraxella sp. only was swabbed and cultured,.

EXAMPLES

Below, the present invention will be explained in detailed through the use of examples. However, this is not intended to limit the scope of present invention to these examples.

Example 1

Using Labyrinthula sp S3-2, a culture was performed in an agar plate medium to which variety of fatty acids or oils were added. The agar plate medium was prepared by dissolving 2.0 g of glucose, 1.0 g of polypeptone, 0.5 g of yeast extract, and 15.0 g of agar in 1 liter of 50% concentration artificial seawater, sterilizing with steam, and after adding 4.5 g of fatty acid such as oleic acid, linoleic acid, α-linolenic acid or soybean oil, apportioning 10 ml each into 9 cm Petri dishes. To the agar plate medium prepared in this way, 100 microliter of culture fluid of Moraxella sp., LB004 strain, is applied and a culture was performed for 3 days at room temperature thereby preparing the Moraxella sp.-applied medium. The culture fluid of Moraxella sp. was one that had been cultured for 4 days in a medium prepared by adding 2.0 g of glucose, 1.0 g polypeptone, and 0.5 g yeast extract to 1 liter of 50% concentration artificial seawater. Labyrinthula isolated strain S3-2 was placed to the center of this Moraxella bacteria coated medium and cultured for 11 days at room temperature. After cultivation, an approximately 2 cm × 2 cm portion of the agar plate medium was excised and transferred to a screw tube, dried for 3 hours at 105° C., thereupon the oil was extracted directly by normal methods or by preparing a fatty acid methyl ester, and then the concentration of LCPUFA was determined. In other words, the dry culture was placed in a screw tube, 10% hydrochloric acid in methanol and dichloromethane was added, and heated for 3 hours in a 60° C. warm bath and after fatty acid methyl esterification of the oil component within the cell, this component was extracted by n-hexane. Using a gas chromatograph, total fatty acid composition of the fatty acid methyl ester was analyzed and the content and composition of the LCPUFA component was determined. Results are shown in table 1. Results for each LCPUFA component were identified by comparison to a control substance with GC/MS analysis.

Labyrinthula sp., S3-2, grew well on each of the fatty acids or oils used in the experiments, growing not only on the surface of the agar medium, but spreading within the agar medium was also observed. At the beginning of the culture, the agar medium was at first a cloudy white due to the fatty acid or oil dispersed throughout the medium, but increased in transparency as the Labyrinthula grew. Growth of the microbes within the medium was confirmed by microscopic observation, indicating that Labyrinthula consumed the dispersed oil. Results of gas chromatography analysis confirmed that the fatty acid which was not present in the dispersed oil was formed and that LCPUFA thereof reached to between 18.3 and 19.2% of the total fatty acids. The principle LCPUFA were DHA and DPA when using various types of fatty acid, whose combined concentration reached a high concentration of around 90%. In the case where soybean oil is used, similarly, DHA and DPA were the main components but the proportion of arachidonic acid increased.

TABLE 1

| Experiment No. | Fatty Acid or Oil | LCPUFA concentration within total fatty acid | LCPUFA* Composition (%) | | | | |
|---|---|---|---|---|---|---|---|
| | | | AA | EPA | DTA | DPA | DHA |
| 101 | Oleic acid | 18.3 | 5.4 | 5.4 | 1.2 | 42.9 | 45.6 |
| 102 | linoleic acid | 19.2 | 1.4 | 2.2 | 0.5 | 44.9 | 50.9 |
| 103 | α-linolenic acid | 19.2 | 2.1 | 1.1 | 1.3 | 43.8 | 51.7 |
| 104 | soybean oil | 18.7 | 18.2 | 5.9 | 2.7 | 35.8 | 37.4 |

*AA: 20:4(n-6), EPA: 20:5(n-3), DTA: 22:4(n-6), DPA: 22:5(n-6), DHA: 22:6(n-3)

Example 2

With medium conditions using soybean oil as in Example 1, cultures were performed under the condition where Moraxella sp. only are applied (M), the condition where Moraxella sp. is not applied and Labyrinthula only are inoculated (Laby), and the condition where both are used (M+Laby) to clarify the effect of Moraxella sp. After culturing for 16 days at room temperature, analysis was performed under analysis conditions shown in experiment 1.

Soybean oil does not contain LCPUFA, as shown in Table 2, when Moraxella sp. only was inoculated, LCPUFA was not detected. When Labyrinthula only are contacted, LCPUFA including DHA was formed, however, by using Labyrinthula together with Moraxella sp., $C_{20-22}$ LCPUFA, including DHA, was produced well from the oleic acid (18:1) or linoleic acid(18:2) contained in the soybean oil, indicating that the conversion to LCPUFA was being really promoted.

TABLE 2

| Experiment No. | Condition | Fatty Acid Composition(%) | | | | | | | | LC-PUFA |
|---|---|---|---|---|---|---|---|---|---|---|
| | | 16:0 | 18:0 | 18:1 | 18:2 | 18:3 | AA | DPA | DHA | |
| 206 | M | 11.1 | 4.1 | 24.2 | 51.4 | 4.6 | 0.0 | 0.0 | 0.0 | 0.0 |
| 207 | Laby | 11.4 | 3.4 | 20.4 | 46.2 | 3.7 | 1.2 | 2.5 | 5.1 | 8.8 |
| 208 | M + Laby | 11.9 | 3.0 | 16.5 | 33.0 | 4.2 | 3.9 | 5.7 | 8.7 | 18.3 |

Example 3

Various strains of Labyrinthula, isolated from fallen mangrove leaves collected at various sites on Ishigaki-jima Island, Ogasawara Island, and the Palau Islands, were cultured for 11 days in the medium having the composition shown in Example 1, with the oil used being soybean oil. After cultivation, an approximately 2 cm×2 cm portion of the agar plate medium was excised and analysis of the LCPUFA within the microbes, and including the oil within the medium, was performed. These results are shown in Table 3.

TABLE 3

| Experiment No. | Strain | LCPUFA conc. in total fatty acid (%) | LCPUFA* Composition (%) | | | | |
|---|---|---|---|---|---|---|---|
| | | | AA | EPA | DTA | DPA | DHA |
| 201 | S3-2 | 10.5 | 20.0 | 7.6 | 3.8 | 31.4 | 37.1 |
| 202 | 714-2 | 14.0 | 19.3 | 0.0 | 8.6 | 22.9 | 49.3 |
| 203 | P11-1 | 11.7 | 14.5 | 4.3 | 1.7 | 18.8 | 60.7 |
| 204 | P28-1 | 9.0 | 13.3 | 4.4 | 3.3 | 33.3 | 45.6 |
| 205 | P37-1 | 10.7 | 15.9 | 5.6 | 3.7 | 29.9 | 44.9 |
| 206 | P38-2 | 9.9 | 22.2 | 9.1 | 5.1 | 30.3 | 33.3 |
| 207 | P47-1 | 11.6 | 22.4 | 9.5 | 4.3 | 32.8 | 31.0 |

*AA:20:4(n-6), EPA: 20:5(n-3), DTA: 22:4(n-6), DPA:22:5(n-6), DHA: 22:6(n-3)

Each of the isolated strains of Labyrinthula exhibited good growth in soybean oil. A value of 9.0-14.0% was obtained for the concentration of LCPUFA within the total fatty acid indicating that LCPUFAs with a carbon number of 20 to 22, including DHA, were produced well from fatty acid with a carbon number of 16 or 18 contained in soybean oil.

Example 4

With the same medium conditions as Example 1, media of various soybean oil concentration were prepared, and cultivation of S3-2 strain was performed. With the conditions of Experiment Nos. 304 to 306, to promote dispersion of soybean oil within the medium, 1 ml/liter of Tween-80 was added as a surfactant. With culture conditions of 7 days at room temperature under the conditions of experiment No. 306 which had the highest concentration of soybean oil, a culture was performed for 14 days. Analysis of the concentration of soybean oil contained in the medium and the amount of LCPUFA formed after cultivation were determined from the peak area of total fatty acid methyl ester by gas chromatography with arachidic acid (20:0) as an internal standard. After preparation of the medium, concentration of soybean oil was from 1.1 mg to 22.8 mg per 1 g of wet agar medium. Results of the culture are shown in Table 4 and the composition of LCPUFA is shown in Table 5.

TABLE 4

| Experiment No. | Soybean Oil Concentration* (mg/g-agar) | Amount of LCPUFA Produced** (mg/g-agar) | LCPUFA Content*** (%) |
|---|---|---|---|
| 301 | 1.1 | 0.10 | 21.6 |
| 302 | 2.2 | 0.23 | 11.6 |
| 303 | 4.9 | 0.22 | 6.7 |
| 304 | 7.9 | 0.37 | 7.1 |
| 305 | 16.4 | 0.56 | 4.5 |
| 306(7d) | 22.8 | 0.39 | 1.7 |
| 306(14d) | 22.8 | 0.76 | 6.9 |

*Soybean Oil Concentration: Concentration (mg) of Soybean oil contained in 1 g of wet agar medium
**Amount of LCPUFA Produced: Total amount of LCPUFA contained in 1 g of wet agar medium after culture
***LCPUFA Content: Content of LCPUFA in total fatty acids.

TABLE 5

| Experiment No. | Soybean Oil Concentration (mg/g-agar) | LCPUFA* Composition (%) | | | | |
|---|---|---|---|---|---|---|
| | | AA | EPA | DTA | DPA | DHA |
| 301 | 1.1 | 15.7 | 4.6 | 0.0 | 43.5 | 36.1 |
| 302 | 2.2 | 24.1 | 6.9 | 9.5 | 29.3 | 30.2 |
| 303 | 4.9 | 35.8 | 7.5 | 9.0 | 14.9 | 32.8 |
| 304 | 7.9 | 25.4 | 11.3 | 0.0 | 25.4 | 38.0 |
| 305 | 16.4 | 26.7 | 4.4 | 6.7 | 31.1 | 31.1 |
| 306(7d) | 22.8 | 29.4 | 11.8 | 5.9 | 23.5 | 29.4 |
| 306(14d) | 22.8 | 15.9 | 2.9 | 5.8 | 37.7 | 37.7 |

The amount of LCPUFA produced with the 7-day culture increased along with an increase in soybean oil concentration but was reduced at a soybean oil concentration of 22.8 mg. On the other hand, the highest value for LCPUFA content of 21.6% was obtained with the condition of the lowest soybean oil concentration. By performing the culture for 14 days with a soybean oil concentration of 22.8 mg, the amount of LCPUFA produced became 0.76 mg/g-agar which was approximately twice that obtained with a 7-day culture and the highest value obtained. Further, the LCPUFA composition also indicated that conversion to fatty acids with a longer chain length and with a higher level of unsaturation, such as DPA and DHA, was increased according as culture period.

As described in detail above, the present invention provides an efficient method for culturing Labyrinthula for which there previously was no effective culturing method. By this method, an oil-containing product comprising long chain polyunsaturated fatty acid having a carbon number of 20 or more and having two or more unsaturated bonds, such as docosahexaenoic acid; or, an oil containing this long chain polyunsaturated fatty acid, can be efficiently produced from plant oil and fatty acid etc. Further, the present invention can be used as a novel method for reforming oil which converts vegetable oil and the like into high value added oil containing long chain polyunsaturated fatty acids.

What is claimed is:

1. An isolated microorganism belonging to the Genus Labyrinthula which produces long chain polyunsaturated fatty acid having a carbon chain number of 20 or more and two or more unsaturated bonds when cultured under appropriate conditions in a medium containing oil or fatty acid as a carbon source.

2. The isolated microorganism according to claim 1, wherein the microorganism belonging to the Labyrinthula genus is Labyrinthula sp S3-2.

3. A culture of one or more microorganisms belonging to the genus Labyrinthula, which is be obtained by culturing the isolated microorganism according to claims 1 or 2 in medium containing oil or fatty acid as a carbon source.

4. A method of producing long chain polyunsaturated fatty acid having a carbon number of 20 or more and two or more unsaturated bonds, comprising culturing at least one of the microorganisms according to claims 1 or 2 under appropriate conditions in a medium containing oil or fatty acid as a carbon source, and collecting long chain polyunsaturated fatty acid from said culture.

* * * * *

UNITED STATES PATENT AND TRADEMARK OFFICE
CERTIFICATE OF CORRECTION

PATENT NO.     : 6,461,839 B2
DATED          : October 8, 2002
INVENTOR(S)    : Toshihiro Yokochi et al.

It is certified that error appears in the above-identified patent and that said Letters Patent is hereby corrected as shown below:

<u>Column 10,</u>
Line 51, please delete "be" after "is."

Signed and Sealed this

Twenty-eighth Day of January, 2003

JAMES E. ROGAN
*Director of the United States Patent and Trademark Office*